(12) United States Patent
Mouradian et al.

(10) Patent No.: US 9,936,885 B1
(45) Date of Patent: Apr. 10, 2018

(54) APPARATUS FOR AMBIENT NOISE CANCELLATION IN PPG SENSORS

(71) Applicant: SENSOGRAM TECHNOLOGIES, INC., Plano, TX (US)

(72) Inventors: Vahram Mouradian, Plano, TX (US); Levon Hovhannisyan, Yerevan (AM); Armen Poghosyan, Yerevan (AM)

(73) Assignee: Sensogram Technologies, Inc., Plano, TX (US)

( * ) Notice: Subject to any disclaimer, the term of this patent is extended or adjusted under 35 U.S.C. 154(b) by 406 days.

(21) Appl. No.: 14/674,499

(22) Filed: Mar. 31, 2015

Related U.S. Application Data

(60) Provisional application No. 61/972,905, filed on Mar. 31, 2014.

(51) Int. Cl.
*A61B 5/1455* (2006.01)
*A61B 5/024* (2006.01)
*A61B 5/021* (2006.01)
*A61B 5/00* (2006.01)

(52) U.S. Cl.
CPC .......... *A61B 5/02416* (2013.01); *A61B 5/021* (2013.01); *A61B 5/14551* (2013.01); *A61B 5/7203* (2013.01)

(58) Field of Classification Search
None
See application file for complete search history.

(56) References Cited

U.S. PATENT DOCUMENTS

| | | |
|---|---|---|
| 4,781,195 A | 11/1988 | Martin |
| 5,713,355 A | 2/1998 | Richardson et al. |
| 5,846,190 A | 12/1998 | Woehrle |
| 5,853,372 A * | 12/1998 | Britton ............... A61B 5/02416 600/485 |
| 5,885,213 A | 3/1999 | Richardson et al. |
| 5,954,644 A | 9/1999 | Dettling et al. |
| 6,385,471 B1 | 5/2002 | Mortz |
| 7,384,398 B2 | 6/2008 | Gagnadre et al. |
| 7,616,110 B2 | 11/2009 | Crump et al. |
| 7,740,591 B1 | 6/2010 | Starr et al. |

(Continued)

FOREIGN PATENT DOCUMENTS

| | | |
|---|---|---|
| WO | 0143624 A2 | 6/2001 |
| WO | 2008109185 A2 | 9/2008 |

OTHER PUBLICATIONS

Addison et al., "Developing an algorithm for pulse oximetry derived respiratory rate (RRoxi): a healthy volunteer study", J. Clin. Monit Comput, 2012, vol. 26, pp. 45-51.

(Continued)

*Primary Examiner* — Eric Winakur
*Assistant Examiner* — Marjan Fardanesh
(74) *Attorney, Agent, or Firm* — RatnerPrestia

(57) ABSTRACT

Disclosed is a PPG signal measurement apparatus comprising a light source for emitting light pulses; a light sensor for receiving reflected light from the light source and generating a sensor signal; an electronic unit including a transimpedance amplifier and an ambient light cancelation unit, a first switch in a front end portion of the light sensor, a second switch in the front end portion of the light sensor, a microcontroller in communication with the light source, the light sensor, and the ambient light cancellation unit.

6 Claims, 2 Drawing Sheets

(56) References Cited

U.S. PATENT DOCUMENTS

| | | |
|---|---|---|
| 7,827,011 B2 | 11/2010 | De Vaul et al. |
| 8,036,842 B2 | 10/2011 | DeVaul et al. |
| 8,313,439 B2 | 11/2012 | McCombie et al. |
| 8,378,811 B2 | 2/2013 | Crump et al. |
| 8,618,930 B2 | 12/2013 | Papadopoulos et al. |
| 8,866,606 B1 | 10/2014 | Will et al. |
| 9,135,699 B2 | 9/2015 | Ralovich et al. |
| 9,396,645 B2 | 7/2016 | Will et al. |
| 9,489,815 B2 | 11/2016 | TenKate |
| 9,526,421 B2 | 12/2016 | Papadopoulos et al. |
| 9,547,977 B2 | 1/2017 | Will et al. |
| 9,640,057 B1 | 5/2017 | Ross |
| 9,704,154 B2 | 7/2017 | Xing et al. |
| 9,773,397 B2 | 9/2017 | Ten Kate et al. |
| 2010/0016738 A1 | 1/2010 | Addison et al. |
| 2014/0142460 A1 | 5/2014 | Zhang et al. |
| 2016/0038044 A1 | 2/2016 | Banerjee et al. |
| 2016/0038061 A1 | 2/2016 | Kechichian et al. |
| 2016/0174913 A1 | 6/2016 | Somanath et al. |
| 2016/0213314 A1 | 7/2016 | Zuckerman-Stark et al. |
| 2017/0172463 A1 | 6/2017 | Papadopoulos et al. |

OTHER PUBLICATIONS

Image of Sensotrack, downloaded Sep. 25, 2016, 1 page.

Meredith et al., "Photoplethysmographic derivation of respiratory rate: a review of relevant physiology", Journal of Medical Engineering & Technology, 2012, pp. 60-66.

George et al., "Respiration Rate Measurement From PPG Signal Using Smart Fusion Technique", International Conference on Engineering Trends and Science & Humanities, 2015, 5 pages.

Burns, "Senso Track Monitors Biometric Health Through Your Ear", downloaded http://www.slashgear.com/sensotrack-monitors-biometric-health-through-your-ear-22351940, Sep. 25, 2016, 8 pages.

Lazaro et al., "Deriving respiration from photoplethysmographic pulse width", Med. Bio. Eng. Comput., 2013, vol. 51, pp. 233-242.

* cited by examiner

APPARATUS FOR AMBIENT NOISE CANCELLATION IN PPG SENSORS

CROSS REFERENCE TO RELATED APPLICATIONS

This application claims the benefit of the filing date of U.S. provisional patent application Ser. No. 61/972,905, filed on Mar. 31, 2014, the disclosure of which is incorporated herein by reference for all purposes.

TECHNICAL FIELD

The present invention relates in general to field of the photoplethysmographic (PPG) measurement system, and in particular to ambient noise cancellation during PPG signal measurement by optical sensors used in pulse oximeters and other devices.

BACKGROUND INFORMATION

The present invention is in the technical field of the photoplethysmographic (PPG) measurement systems and apparatus using optical sensors. More particularly, the present invention is in the technical field of ambient noise cancellation during PPG signal measurement by optical sensors used in pulse oximeters and other devices).

Photoplethysmography is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue-where blood perfuses the tissue, and photoelectrically senses the absorption of light in such tissue. The changing light characteristics can be measured and used to determine the heart rate of a patient and other parameters (blood oxygen saturation SpO2, respiration rate, blood pressure, etc.).

In the field of photoplethysmography, light pulses from different portions of electromagnetic spectrum are used to noninvasively determine various blood values. Typically PPG measurement systems, such as pulse oximeters, include an optical sensor for releasable attachment to the tip of patient's appendage (e.g., a finger, earlobe and others). The sensor directs light signals into the appendage where the sensor is attached. Some portion of light is absorbed and a remaining portion passes through patient tissue. The intensity of light passing through the tissue is monitored by a sensor. The intensity related signals produced by the sensor are used to compute blood parameters.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. The tissue of these body portions is perfused with blood and the tissue surface is readily accessible to the sensor.

One problem with oximeter measurements is that in addition to receiving the light that was directed at the tissue, ambient light is also detected by the photodetector. Attempts can be made to block out ambient light, but some amount of ambient light will typically be detected. One particular concern is the light at the power line frequency of fluorescent or other lights, which is 60 Hz in the United States and 50 Hz in Europe and other countries.

Since a single photodetector is typically used, the light of different wavelengths, such as red and infrared, is time multiplexed. The detected signal must be demultiplexed. The demultiplexing frequency must be high enough so that it is much larger than the pulse rate. However, choosing a demultiplexing frequency is also impacted by the ambient light interference.

The measured signals can be distorted by various ambient noises (optical and electrical), thus resulting in potential measurement errors. Device manufacturers employ various sampling and timing strategies, which usually contain an ambient light sample, during which neither of deployed LEDs is powered. This ambient light level is measured and later subtracted from the signal. The drawback of this approach is in the overload of the receiver at certain supply voltage levels, which may limit the gain of the useful signal. This usually makes the measurement invalid and obsolete. Also, the cost and area for electronics component deployment may be significantly larger.

One problem in these solutions is that the ambient light signal and useful light signal both are amplified by the first current-voltage (transimpedance) amplifier. In this case, due to limited voltage used in mobile and wearable devices the signal to noise ratio (SNR) may be dramatically decreased.

What is needed, therefore, is a device to increase the SNR in PPG measurement systems.

SUMMARY

In response to these and other problems, in one embodiment, there is a PPG signal measurement method and apparatus which provides (1) a canceling the ambient noises (light and electrical) in the measured PPG signals and also (2) a significantly increasing a signal-noise ratio in wearable/mobile devices.

In another aspect of the invention, dark signal, or ambient light, level are fixed using very short time just before each of the light emitter wavelengths (red and infrared in one embodiment). This compensates for a variation in ambient light during the detected signal (since the signal time is also very short).

These and other features, and advantages, will be more clearly understood from the following detailed description taken in conjunction with the accompanying drawings. It is important to note the drawings are not intended to represent the only aspect of the invention.

DETAILED DESCRIPTION

Specific examples of components, signals, messages, protocols, and arrangements are described below to simplify the present disclosure. These are, of course, merely examples and are not intended to limit the invention from that described in the claims. Well-known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art. Details regarding control circuitry or mechanisms used to control the rotation of the various elements described herein are omitted, as such control circuits are within the skills of persons of ordinary skill in the relevant art.

Disclosed aspects may be used in photoplethysmographic measurement apparatus to improve PPG pulse-signal quality by cancellation of ambient optical and electrical noises. For these purposes, the measurement instrument will be described in terms of a PPG optical sensor which noninvasively measures various blood values, such as heart rate, blood oxygen saturation, blood pressure, etc.

Figure 1:
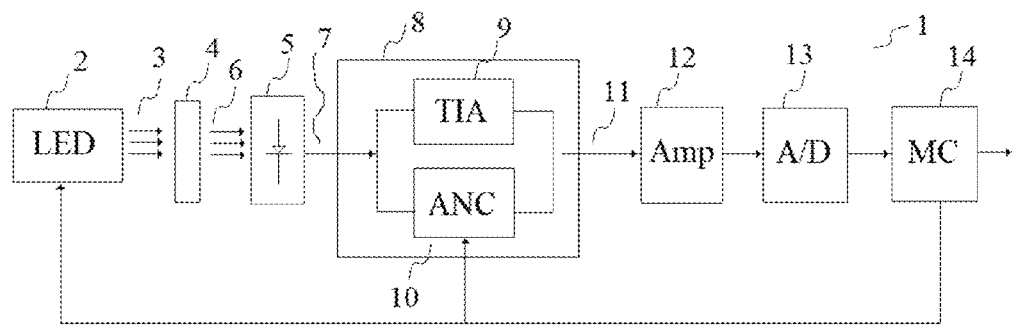
FIG. 1 shows a schematic block diagram of an embodiment of a proposed PPG signal measurement apparatus.

Turning now to FIG. 1, there is presented one embodiment of a schematic block diagram of a PPG signal measurement apparatus 1. The PPG signal measurement apparatus 1 comprises a light source 2 (e.g. an LED) for emitting light pulses 3 into tissue 4 of a living being, in particular a person. In certain embodiments, the light source 2 may, e.g., be mounted on a finger, ear clip, or a watch worn by the living being. The apparatus 1 further includes a light sensor 5 (e.g. a photodiode) for receiving light 6 from the tissue 4 and generating a sensor signal 7 (e.g. a photodiode current).

A combination unit 8 receives the sensor signal 7. In certain embodiments, the combination unit 8 cancels ambient noise in the sensor signal 7 and produces a current-to-voltage amplified signal from the sensor signal 7. The combined unit 8 includes a transimpedance amplifier (TIA) 9 and an ambient noise cancelation unit 10. The combined unit 8 receives the sensor signal 7 and transforms the signal into a clear or clearer amplified sensor signal 11 (e.g. for amplifying the photodiode current into a voltage signal without or with reduced ambient noises).

The processed signal 11 may be then be received by additional signal processing units, such as an additional amplifier 12, analog-digital converter 13 and microcontroller 14.

Figure 3:
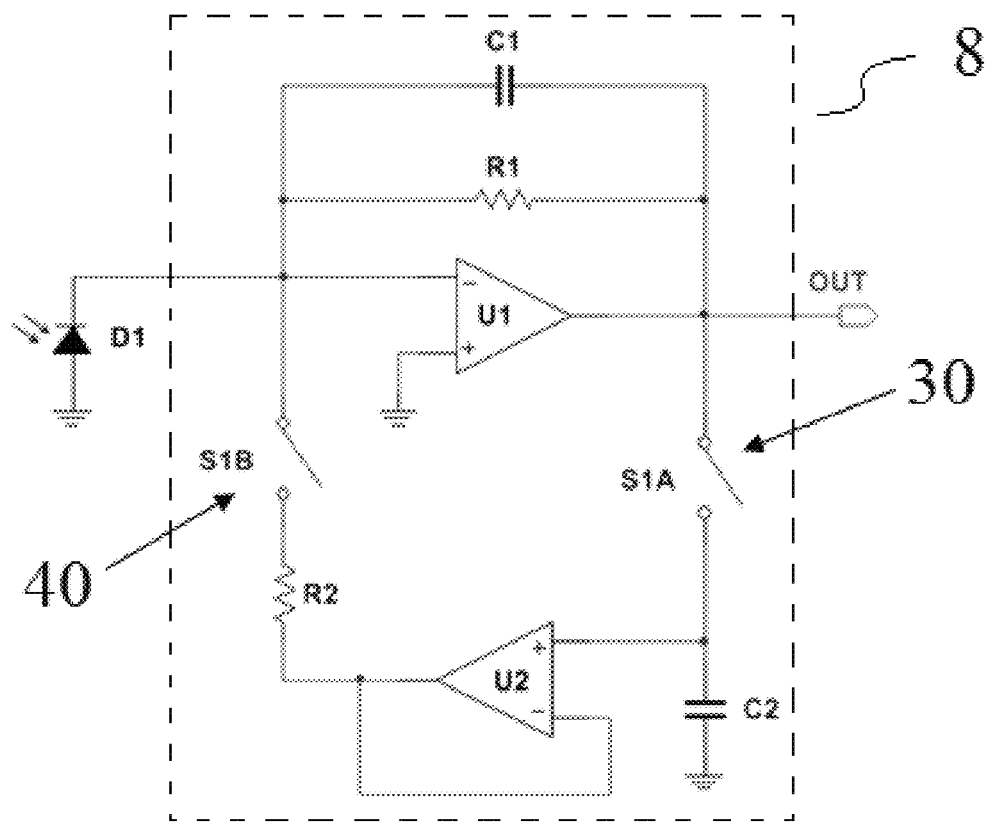
FIG. 3 is the electrical diagram of the front-end of the PPG sensor according to an embodiment of the present invention.

In certain embodiments, the microcontroller 14 may be configured to control the light source 2 and the combination unit 8, e.g. the ambient light cancelation unit 10 and the transimpedance amplifier 9 (FIG. 3). In certain embodiments, such that a first switch 30 in a front end portion of the combination unit 8 may be only switched on during time periods while the light source 2 is switched off and that a second switch 40 in the front end of the combination unit 8 is only switched on during time periods while the light source 2 is switched on. Details regarding the front end of the combination unit 8 will be discussed below in reference to FIG. 3.

Figure 2:
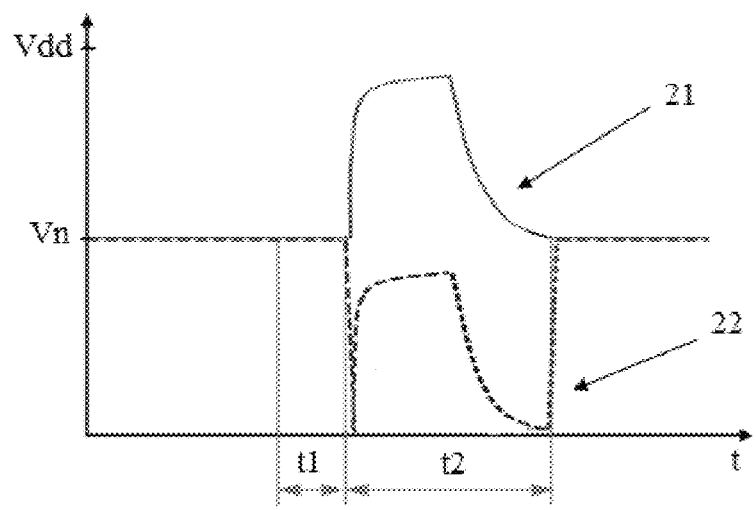
FIG. 2 is a diagram illustration the ambient light cancellation: 1- PPG pulse signal with ambient light noise, 2- clear pulse signal after the ambient light noise cancellation.

Referring now to FIG. 2, there is a graph of conventional signal (or pulse waveform) with ambient light noise measured by a photodetector as a function of time. The pulse waveform is produced by a pulse PPG optical sensor as a result of light signal radiated by LED with corresponding wavelength and ambient optical and/or electrical noises. The waveform 21 represents a PPG pulse signal with ambient light noise. The waveform 22 represents a PPG pulse signal after the ambient light noise cancellation or reduction (e.g., a clear signal). Thus, FIG. 2 is a time diagram of a PPG sensor (sensor 5) response to the ambient light cancellation process.

FIG. 3 is an electrical diagram of the front-end of the PPG sensor (sensor 5) implementing one embodiment of the ambient noise cancellation process. FIG. 3 shows the electronic building blocks used in a PPG measurement system, a transimpendence (current-to-voltage) amplifier stage, that converts light intensity at the photodiode (D1) into an amplifier output voltage ($V=I \times R$, transimpendence gain is proportional to the feedback resistor value R1).

The diagram suggested disclosed aspects allow cancellation the ambient noises and obtaining clear PPG pulse signal (graph 2, FIG. 2). The principle is that during the time period t1 (before LED is turned on) the switch 30 is turned on. During this time period the capacitor C2 is charged. When the LED is turned on, the switch 30 is turned off and the switch 40 is turned on, so the capacitor C2 is discharged. The capacitor C2 acts as a voltage drop proportional to the light when no LEDs are turned on. As a result a clear pulse signal (graph 21, FIG. 2) from LED light during pulse time period t2 is measured with ambient noise cancellation. So there is no necessity to measure ambient light level for further subtraction, and the signal value is always in the amplifier range. The typical ranges of t1 and t2 time periods are 2-10 us and 20-150 us correspondingly and R1=R2=1 MOhm.

In certain embodiments, a dark signal, or ambient light level detection process uses a very short time period t1 (<10 us) just before each of the light emitter wavelengths (red and infrared in one embodiment) to compensate for a variation in ambient light during the detected signal.

Thus, an improved photoplethysmographic measurement system is disclosed in which a portion of a time division multiplexed (TDM) signal represents an ambient light level, and other TDM signal portions represent detected levels of two or more centered wavelengths of transmitted light. The ambient light portions of the signal are effectively canceled from detected light portion before they are sent as inputs of an instrumentation amplifier(s) so as to produce a continuous output voltage that is proportional to a difference in signal levels between the ambient and detected light portions of a TDM signal.

Such an approach provides for ambient light level subtraction with reduced noise and allows to use all diapason of current-voltage transimpedance amplifier thus increasing significantly SNR and allowing only the useful optical signal to be received by the optical measurement system. Such apparatus and method allow increase and enhance the performance of the sensor.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

What is claimed is:

1. A PPG signal measurement apparatus comprising:
   a light source for emitting light pulses;
   a light sensor for receiving reflected light from the light source and generating a sensor signal;
   a combination unit electrically coupled to the light sensor, the combination unit including:
   an ambient light signal cancelation unit including a first switch, and a second switch, and
   a transimpedance amplifier; and
   a microcontroller in communication with the light source, the light sensor, and the combination unit, the microcontroller being configured to switch on the first switch only during a first time period while the light source is switched off and switch on the second switch only during a second time period while the light source is switched on;
   wherein the ambient light signal cancellation unit comprises a first capacitor and a voltage following amplifier configured to cancel an ambient light signal before the ambient light signal is processed by the transimpedance amplifier to provide an amplified analog sensor signal with an increased signal-to-noise ratio.

2. The PPG signal measurement apparatus of claim 1, wherein the microcontroller includes additional instructions to control the light source and the ambient light cancelation unit such that the first time period is within 10 µs before the light source is switched on.

3. The PPG signal measurement apparatus of claim 1, wherein the first switch is connected to an output side of the transimpedance amplifier and the second switch is connected to an input side of the transimpedance amplifier.

4. The PPG signal measurement apparatus of claim 3, wherein a first pole of the first switch is connected between the output side of the transimpedance amplifier and a second pole of the first switch is connected in parallel to the first capacitor and an input side of the voltage following amplifier.

5. the PPG signal measurement apparatus of claim 4, wherein a first pole of the second switch is connected to the input side of the transimpedance amplifier and a second pole of the second switch is connected to an output side of the voltage following amplifier.

6. A PPG signal measurement apparatus comprising:
   a light source for emitting light pulses;
   a light sensor for receiving reflected light from the light source and generating a sensor signal;
   a combination unit electrically coupled to the light sensor, the combination unit including:
   an ambient light signal cancelation unit including a first switch, and a second switch, and
   a transimpedance amplifier; and
   a microcontroller in communication with the light source, the light sensor, and the combination unit, the microcontroller being configured to switch on the first switch only during a first time period while the light source is switched off and switch on the second switch only during a second time period while the light source is switched on; wherein the ambient light signal cancellation unit comprises means for canceling an ambient light signal before the ambient light signal is processed by the transimpedance amplifier to provide an amplified analog sensor signal with an increased signal-to-noise ratio.

* * * * *